(12) United States Patent
Millard et al.

(10) Patent No.: US 8,932,646 B2
(45) Date of Patent: Jan. 13, 2015

(54) PEROXIDE CONTACT LENS CARE SOLUTION

(75) Inventors: Kimberly Anne Millard, Rochester, NY (US); Erning Xia, Penfield, NY (US); Suzanne F. Groemminger, Rochester, NY (US); Jenilee Kilbury, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 761 days.

(21) Appl. No.: 13/012,018

(22) Filed: Jan. 24, 2011

(65) Prior Publication Data

US 2011/0311646 A1 Dec. 22, 2011

Related U.S. Application Data

(60) Provisional application No. 61/356,122, filed on Jun. 18, 2010.

(51) Int. Cl.
*A61L 12/12* (2006.01)
*C11D 3/00* (2006.01)
*C11D 7/06* (2006.01)
*C11D 7/32* (2006.01)
*C11D 3/39* (2006.01)

(52) U.S. Cl.
CPC ............ *A61L 12/124* (2013.01); *C11D 3/0078* (2013.01); *C11D 7/06* (2013.01); *C11D 7/3218* (2013.01); *C11D 7/3245* (2013.01); *C11D 7/3272* (2013.01); *C11D 3/3947* (2013.01)
USPC ......................................................... 424/616

(58) Field of Classification Search
CPC .............................. A61K 33/40; A61L 12/124
See application file for complete search history.

(56) References Cited

U.S. PATENT DOCUMENTS

| | | | |
|---|---|---|---|
| 3,912,451 A * | 10/1975 | Gaglia, Jr. ...................... 422/30 |
| 4,588,586 A | 5/1986 | Kessler et al. |
| 4,812,173 A | 3/1989 | Tsao et al. |
| 4,889,689 A | 12/1989 | Tsao |
| 5,089,240 A | 2/1992 | Perlaky |
| 5,196,174 A * | 3/1993 | Cerola et al. .................. 422/300 |
| 5,209,865 A | 5/1993 | Winterton et al. |
| 5,306,352 A | 4/1994 | Nicolson et al. |
| 5,523,012 A | 6/1996 | Winterton et al. |
| 5,869,532 A | 2/1999 | Mizushima et al. |
| 7,022,654 B2 | 4/2006 | Tsao |
| 2004/0120916 A1 * | 6/2004 | Huth ........................ 424/70.13 |
| 2008/0185298 A1 | 8/2008 | Kanner et al. |
| 2011/0114517 A1 * | 5/2011 | Minick et al. ................. 206/223 |

FOREIGN PATENT DOCUMENTS

| | | |
|---|---|---|
| JP | 11052309 | 2/1999 |
| WO | WO 96/03157 A1 | 2/1996 |
| WO | WO9603157 A1 | 2/1996 |
| WO | WO 2008/077106 A1 | 6/2008 |

OTHER PUBLICATIONS

International Search Report, "PCT/US2011/022655," Peroxide Contact Lens Care Solution, Apr. 2011.

* cited by examiner

*Primary Examiner* — Abigail Fisher
*Assistant Examiner* — Jessica Kassa
(74) *Attorney, Agent, or Firm* — Toan P. Vo

(57) ABSTRACT

A contact lens disinfecting solution that comprises 0.5 wt. % to 6 wt. % hydrogen peroxide, or a chemical precursor of hydrogen peroxide, and a P-metal modulating compound. The presence of the P-metal modulating compound in the disinfecting hydrogen peroxide solution slows the rate at which the hydrogen peroxide is neutralized, particularly during the initial two hours, by a catalyst element that includes a P-metal. This reduction in rate of peroxide neutralization provides a more effective solution for killing certain microorganisms and fungi.

8 Claims, 8 Drawing Sheets

PEROXIDE CONTACT LENS CARE SOLUTION

This application claims the benefit under 35 U.S.C. §119(e) of U.S. provisional application Ser. No. 61/356,122 filed Jun. 18, 2010, the entire disclosure of which is incorporated herein by reference.

FIELD OF THE INVENTION

The invention relates to compositions and methods for cleaning and disinfecting contact lenses, particularly, soft hydrogel contact lenses.

BACKGROUND OF THE INVENTION

Disinfecting solutions for the care of contact lenses are well known in the art and the use of such lenses and solutions often involves a daily disinfecting regimen. The present market of lens care solutions includes multipurpose solutions, which include one or more antimicrobial components, and solutions that include about 3 wt. % hydrogen peroxide. One apparent advantage of a hydrogen peroxide lens care disinfecting system is the absence of a disinfecting agent in the solution or the lens following neutralization of the hydrogen peroxide with the exception of residual amounts of hydrogen peroxide, generally less than 100 ppm.

In general, the hydrogen peroxide systems include a disinfecting solution that contains hydrogen peroxide into which previously worn contact lenses are placed and allowed to remain in contact with the solution for a specified period of time. The hydrogen peroxide is believed to (1) oxidize chloride in the bacteria to hypochlorite or (2) decompose into nascent oxygen and hydroxyl radicals, thus providing an antimicrobial effect. Following or simultaneous with this disinfection cycle the peroxide solution requires neutralization, and this can be carried out either by catalytic reduction with a supported platinum catalyst or with an enzyme such as catalase. Following neutralization the contact lens may be reinserted into the eye without a separate rinse step as the hydrogen peroxide has been neutralized to levels that are non-irritating to ocular tissues.

Consumer friendly, single step peroxide disinfection systems have achieved near exclusive popularity, e.g., the AO Sept system by CibaVision and the EZ Sept system by Bausch & Lomb. These two systems operate by placing a contact lens to be disinfected in contact with a solution of peroxide and a platinum disk whereby peroxide disinfection and peroxide neutralization occur essentially simultaneously. The user places the lenses in the lens holding compartments, adds the disinfecting solution to the system container, closes the container placing the lenses in contact with the solution and waits the appropriate time interval, typically four to eight hours, before removing the lenses from the disinfection system. The lenses can then be directly inserted onto the eye.

In hydrogen peroxide systems that rely upon a platinum catalyst, the hydrogen peroxide in solution is neutralized relatively quite rapidly. Consequently, lens disinfection at the higher peroxide concentrations is somewhat limited in time. For example, in an AO Sept system in which the initial concentration of hydrogen peroxide is 3%, it is said that the concentration of the hydrogen peroxide falls rapidly to about 0.1% in about 12.5 minutes. See, U.S. Pat. No. 5,306,352. After this point, the neutralization of the remaining hydrogen peroxide proceeds relatively slowly and it takes several hours, i.e. up to 8 hours or more, before the hydrogen peroxide is depleted sufficiently so that the contact lens can be inserted onto the eye without fear of irritation or injury.

U.S. Pat. No. 5,306,352 to Nicolson et al. recognizes the need to control the catalytic decomposition or neutralization reaction of the hydrogen peroxide such that concentration of the hydrogen peroxide remains at higher levels during the initial stages of neutralization, yet maintain the necessary degree of neutralization to allow for direct insertion of the disinfected lens onto the eye without the need for rinsing the lenses. In FIG. 1 the hydrogen peroxide neutralization rate of the AO Sept system is plotted in which a platinum catalyst is contacted with a 3% hydrogen peroxide solution. In such situation, it is noted that the concentration of the hydrogen peroxide falls rapidly to about 0.1% in about 12 minutes. FIG. 2 represents a decomposition profile of a hydrogen peroxide system in which the rate of decomposition of the hydrogen peroxide is said to be controlled by means described by Nicolson.

Nicolson lists five general steps one could consider in the catalytic decomposition of hydrogen peroxide: (1) the transportation of the hydrogen peroxide to the catalyst to insure a continuous contact between the catalyst and hydrogen peroxide; (2) the absorption of hydrogen peroxide to the catalyst surface; (3) the neutralization or catalysis in which the hydrogen peroxide is decomposed to water and nascent oxygen; (4) the desorption from the surface of the reaction products, i.e. the water and nascent oxygen, or other contaminants so as to expose the active sites; and (5) the transportation of the reaction products away from the catalytic surface. Nicolson does not, however, clearly describe how one of skill might actually control any one of these reaction (neutralization) stages to achieve a desired neutralization curve.

With respect to step (3), Nicolson proposes that the catalyst be partially poisoned in the manufacturing setting prior to sale and first use by the consumer. To determine whether the catalyst is sufficiently pre-poisoned, the generation of oxygen from the system can be measured. As stated, in a typical AO Sept system using platinum as a catalyst one can estimate the rate of neutralization from the initial generation of oxygen at about 40 mL/min. Nicolson proposes that the catalyst be sufficiently pre-poisoned so that the amount of oxygen liberated during the reaction is periodically measured until the oxygen liberation rate is somewhere between 2 and 15 mL/min, and preferably between 2 and 5 mL/min. Again, there is no description in Nicolson as to how one might pre-poison a platinum catalyst to achieve the proposed peroxide neutralization rate.

Instead, Nicolson focuses on a mechanical/chemical means referred to as a "buoyance mediated control system" to delay hydrogen peroxide neutralization in contact lens disinfecting systems. It is stated that the absorption of generated oxygen gas provides a neutralizing catalytic particle sufficient buoyancy to rise to the surface of the peroxide solution. Buoyancy controlled catalytic reactions fall into two primary types of reactions. First are those reactions which generate a gas. The gas bubbles adhere to the surface of the catalyst particle creating a buoyant particle. The buoyant particle rises to the surface where the gas bubble escapes to the gas phase over the liquid reaction medium. Upon losing the gas bubbles, the catalyst loses buoyance and begins to descent until it again contacts liquid containing reactants so that further buoyant gas bubbles can be generated. This bobbing action is, therefore, confined to the uppermost layers of the solution leaving the lower portion of the solution in a relatively non-neutralized state for a greater period of time. One perceived problem with the floating particle method is preventing the particles from adhering to the lenses, and thereby, avoiding the need for a separate rinse solution.

In the second type of buoyancy controlled catalytic reaction, the catalytic particle resides at or near top of the solution due to its density. If the reaction product solution is less dense than the reactant solution, then the reaction proceeds substantially from top to bottom and the catalytic particles are designed to be slightly less dense than the reactant solution (i.e. between the reaction product and reactant solution densities). If the reaction product solution is more dense than the reactant solution, then the reaction proceeds from bottom to top and the catalytic particle is designed to be slightly more dense than the reactant solution. In either event, the catalytic particle must return to contact the reactant solution if the neutralization reaction is to proceed. In either case, these buoyancy controlled processes are very complex and impose substantial limitations on commercial viability or applications.

The presently marketed peroxide disinfection systems have been around for over twenty-five years with little or no improvement in disinfection profile. Surfactants have been added to assist in protein and lipid cleaning, but little, if any, progress has been made to improve upon the biocidal effectiveness of lens care peroxide systems. Neither have there been any advances in a peroxide disinfectant system that makes it possible to control the neutralization rate of the hydrogen peroxide. There is a need to address these drawbacks in the currently marketed lens care peroxide systems, and to improve upon the disinfection and effective storage of the lenses after complete neutralization of the hydrogen peroxide.

SUMMARY OF THE INVENTION

The invention is directed to a contact lens disinfecting solution comprising: 0.5 wt. % to 6 wt. % hydrogen peroxide or a chemical precursor of hydrogen peroxide; and a P-metal modulating compound. The solution exhibits a pseudo first-order, half-life of hydrogen peroxide over an initial sixty minutes of neutralization from 13 minutes to 30 minutes, as measured in a given hydrogen peroxide, contact lens disinfection case equipped with a catalyst comprising a P-metal.

The invention is also directed to a contact lens disinfecting solution comprising: 0.5 wt. % to 6 wt. % hydrogen peroxide or a chemical precursor of hydrogen peroxide; and a P-metal modulating compound. The disinfecting solution exhibits a hydrogen peroxide neutralization profile that is more effective against Candida albicans or Serratia marcescens by 0.5 log-kill or greater after an initial four hours of neutralization with a catalyst comprising a P-metal than an equivalent contact lens disinfecting solution but without the P-metal modulating compound. Also, the disinfecting solution will have an osmolality value of from 150 mOsmol/kg to 500 mOsmol/kg following neutralization of the hydrogen peroxide.

The invention is also directed to a contact lens disinfecting solution comprising:

0.5 wt. % to 6 wt. % hydrogen peroxide or a chemical precursor of hydrogen peroxide; and a P-metal modulating compound of general formula I

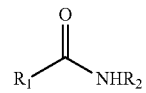

wherein $R_1$ is $C_1$-$C_6$alkyl, —$(CH_2)_n CH(^+NH_3)(CO_2^-)$ and n is 1 or 2, or $NHR_3$; and $R_3$ is H or $R_2$, and $R_2$ is H, OH or $C_1$-$C_6$alkyl; with the proviso that if $R_1$ is $NHR_3$ and $R_2$ and $R_3$ are H then the molar concentration of the P-metal modulating compound is less than the molar concentration of the hydrogen peroxide in the disinfecting solution.

The invention is also directed to a contact lens disinfecting solution comprising:
0.5 wt. % to 6 wt. % hydrogen peroxide or a chemical precursor of hydrogen peroxide; and a P-metal modulating compound with one or two nitrogen atoms and one to six carbon atoms, wherein the molar concentration of the P-metal modulating compound is less than the molar concentration of the hydrogen peroxide in the disinfecting solution.

The invention is also directed to a contact lens disinfecting solution comprising:
0.5 wt. % to 6 wt. % hydrogen peroxide or a chemical precursor of hydrogen peroxide; and a P-metal modulating compound. The solution has a pseudo first-order, half-life of hydrogen peroxide over an initial sixty minutes of neutralization that is 1.25 times to 3 times greater with the P-metal modulating compound in the solution than in the absence of the P-metal modulating compound. The half-life value is determined for a given hydrogen peroxide, contact lens disinfection case equipped with a catalyst comprising a P-metal.

BRIEF DESCRIPTION OF THE DRAWINGS

The invention will be better understood from the following description and in consideration with the accompanying Figures. It is to be understood, however, that each of the Figures is provided to further illustrate and describe the invention and is not intended to further limit the invention claimed.

DETAILED DESCRIPTION OF THE INVENTION

Figure 1:
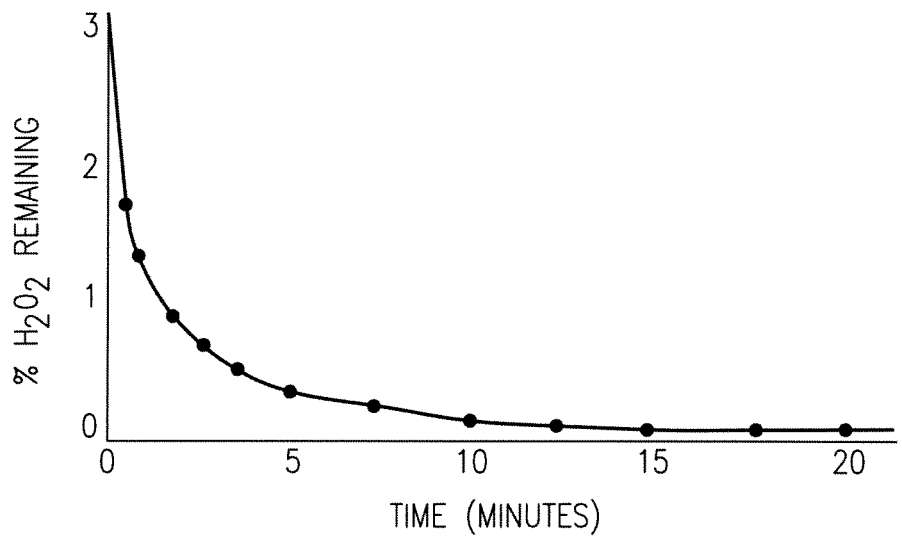
FIG. 1 is a neutralization rate profile of a peroxide disinfecting solution of the prior art.
Figure 2:
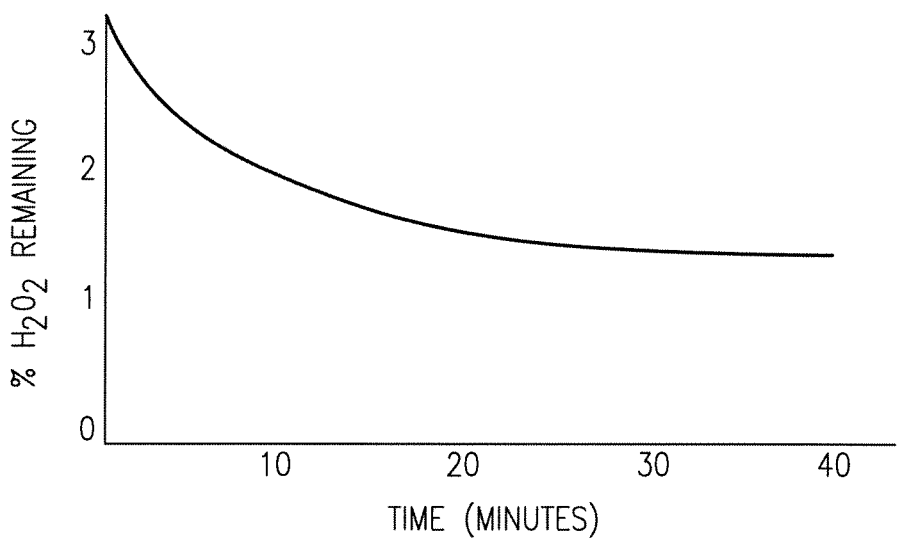
FIG. 2 is a neutralization rate profile of a proposed peroxide disinfecting system of the prior art.
Figure 3:
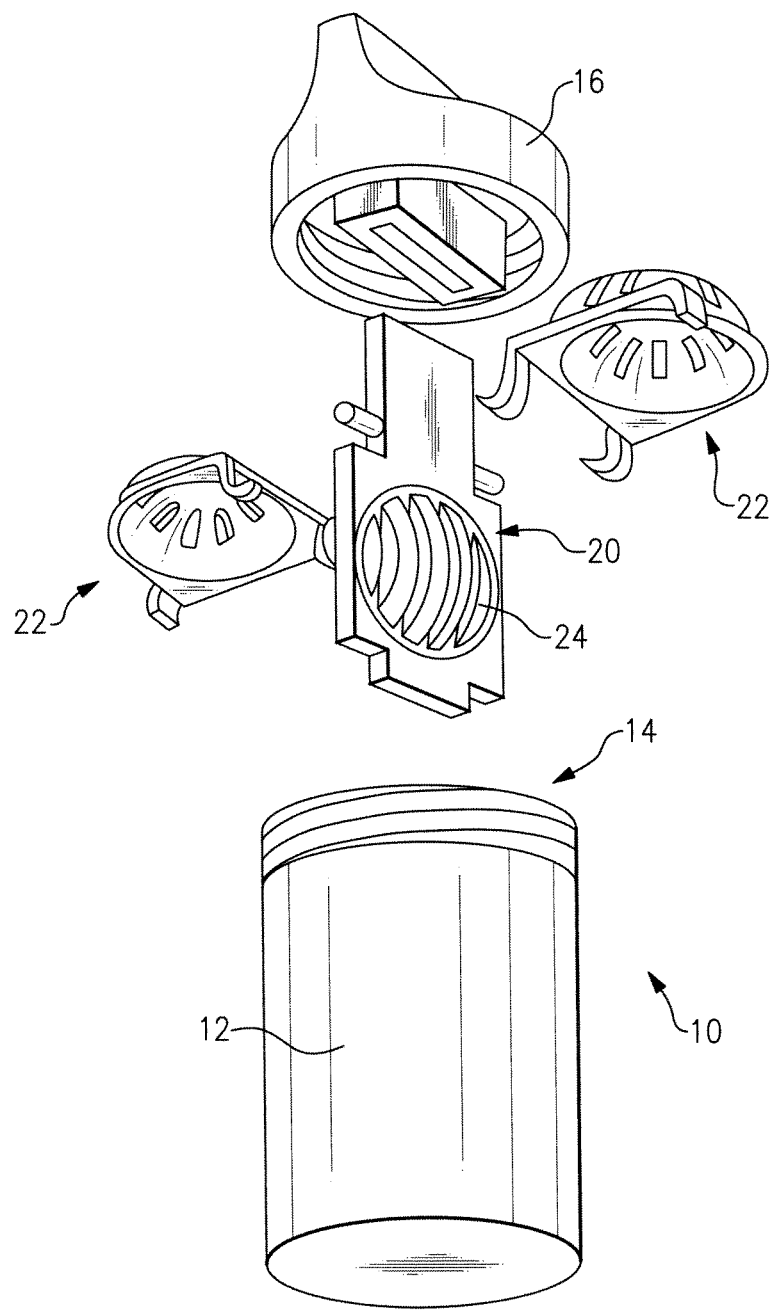
FIGS. 3 and 4 are prior art lens cases for cleaning and disinfecting contact lenses using a peroxide disinfecting solution.

Contact lens disinfecting systems designed for use with peroxide-based, contact lens disinfecting solutions are well known. U.S. Pat. No. 5,196,174 to Cerola et al. and U.S. Patent Pub. No. 20080185298 to Kanner et al. describe such systems, the entire disclosures of which are incorporated herein by reference. As shown in FIG. 3 the contact lens disinfecting apparatus 10 includes a container or reaction vessel 12, which is generally cylindrical in shape and terminates in an open top 14 which preferably has a thread for engaging a complementary thread formed within a cap member 16. This reaction vessel or container 12 is particularly adapted to contain a quantity of an aqueous peroxide disinfecting solution. In accordance with prevailing practice, the hydrogen peroxide is of a relatively low concentration, and preferably no more than a 6 wt. % solution of hydrogen peroxide. The cap member 16 includes a lens supporting assembly 20. As shown, the lens supporting assembly 20 comprises a pair of basket-type lens support structures 22. Each lens supporting assembly comprises a base that includes a lens-supporting dome or semi-spherical portion 24 complementary to the lens support structures 22.

Figure 4:
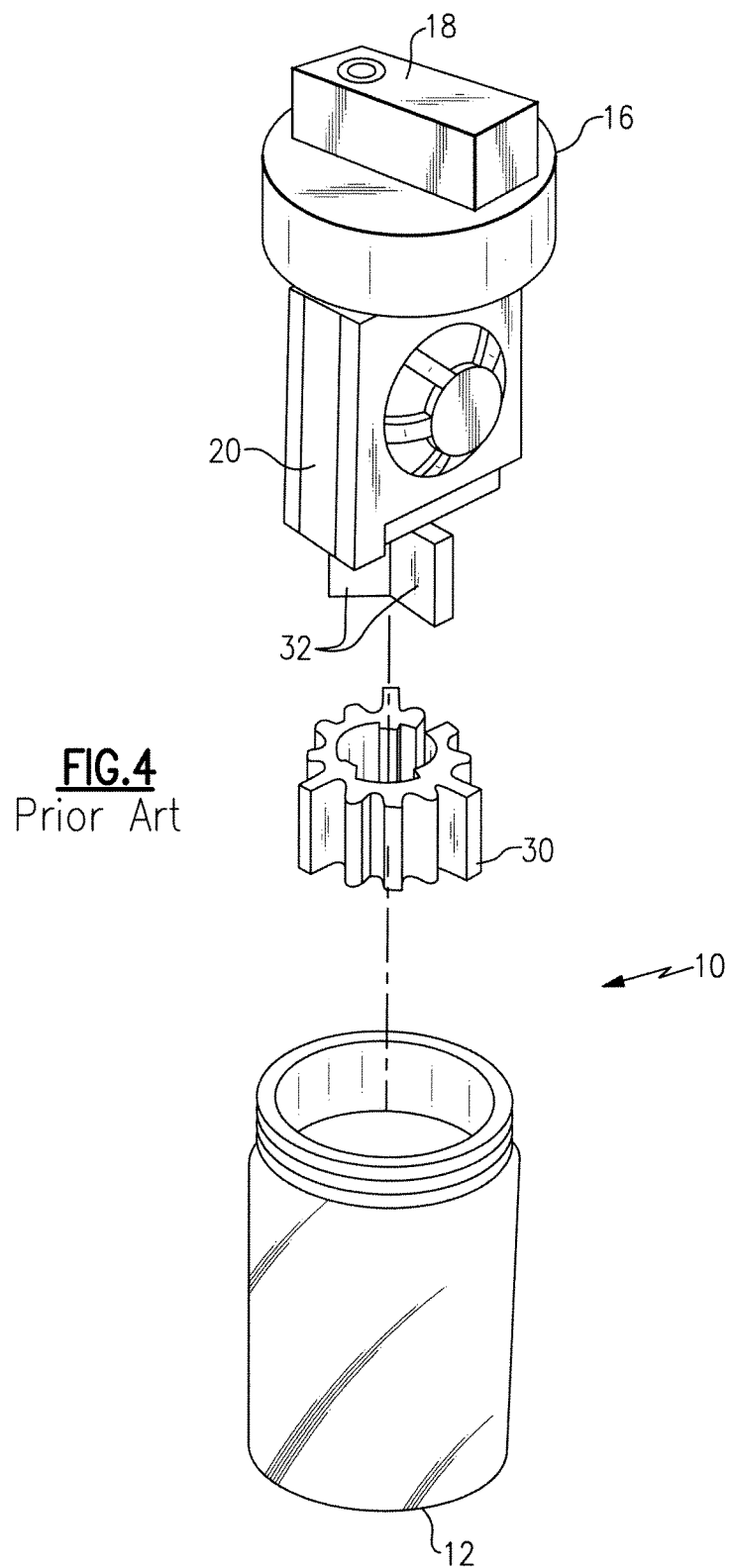

As shown in FIG. 4, the contact lens disinfecting apparatus 10 also includes a catalytic element 30 such as a platinum coated substrate that catalyzes the decomposition of the hydrogen peroxide in the disinfecting solution to nascent oxygen and water. The catalytic element 30 can be attached to a connecting member 32 proximate to an end of the lens supporting assembly 20 opposite from cap member 16. Preferably, the peroxide decomposition or neutralization process is arranged to occur over a period of several hours, e.g., from 2 to 6 hours, depending on the nature of the catalytic element and the initial concentration of the hydrogen peroxide in the disinfecting solution. Generally, it is recommended that the consumer conduct the neutralization process overnight in order to assure full decomposition of the hydrogen peroxide. Cap member 16 also includes a gas venting member 18 which enables the oxygen produced during the peroxide neutralization reaction to escape the closed lens case.

The term P-metal refers to the catalytic transition metals that are positioned on a substrate (to form a catalytic element), and thereby, facilitate the catalytic neutralization of hydrogen peroxide in the contact lens disinfecting solution. The P-metals are platinum or palladium. It is also understood, that one can position both platinum and palladium on a lone substrate to facilitate the catalytic neutralization of hydrogen peroxide. Processes to position the P-metals on a substrate to form a catalytic element are well known in the art, and include physical sputtering, PVD and CVD. Presently, contact lens cases packaged with hydrogen peroxide, contact lens disinfecting solutions include a catalytic element that includes platinum.

The present invention is directed to a contact lens disinfecting solution comprising:
0.5 wt. % to 6 wt. % hydrogen peroxide, or a chemical precursor of hydrogen peroxide; and a P-metal modulating compound. The presence of the P-metal modulating compound in the disinfecting hydrogen peroxide solution slows the rate at which the hydrogen peroxide is neutralized, particularly during the initial two hours, by a catalyst element that includes a P-metal. This reduction in rate of peroxide neutralization provides a more effective solution for killing certain microorganisms and fungi. The disinfecting peroxide solutions are effective against a wide spectrum of microorganisms, including but not limited to *Staphylococcus aureus*, *Pseudomonas aeruginosa*, *Serratia marcescens*, *Candida albicans*, and *Fusarium solani*. The inventive solutions are particularly effective against *Candida albicans* or *Serratia marcescens* as evidenced by 0.5 log-kill or greater than an equivalent contact lens disinfecting solution but without the P-metal modulating compound.

The overall antimicrobial effect for a tested solution is determined by adding $1\times10^5$ to $1\times10^6$ microbes into a lens case filled with 10 mL of a test solution. The lens case was closed with a cap to which is attached a cap stem with a catalytic disk immediately after the introduction of the microbes. Kill was measured by log reduction at 4 or 6 hours and 24 hours. See Example section (pages 18-20) for more experimental details on determining the biocidal effectiveness for the described peroxide lens care solutions.

The term "hydrogen peroxide" includes a stabilized form of hydrogen peroxide. Exemplary stabilized forms of hydrogen peroxide are described in U.S. Pat. Nos. 4,812,173 and 4,889,689, the entire disclosures of which are incorporated herein by reference. The term "a chemical precursor of hydrogen peroxide" is a chemical compound that dissociates in water to form an aqueous hydrogen peroxide solution, wherein the amount of dissociative hydrogen peroxide following complete dissociation is from 0.05 wt. % to 6 wt. %. Exemplary chemical precursors of hydrogen peroxide include sodium perborate, sodium percarbonate, urea hydrogen peroxide and sodium perpyrophosphate. It is of course understood by those of skill in the art that the described peroxide lens care solutions can include both a stabilized form of hydrogen peroxide and a chemical precursor of hydrogen peroxide, however, the total concentration of hydrogen peroxide does not exceed 6 wt. %

In one or more preferred embodiments, the molar concentration of hydrogen peroxide is at least two times greater than the molar concentration of P-metal modulating compound in the solution providing a molar ratio of hydrogen peroxide to P-metal modulating compound of at least 2:1. Exemplary molar ratios of hydrogen peroxide to P-metal modulating compound in the solution are from at least 5:1, at least 15:1, at least 50:1 and at least 80:1. An exemplary range of a molar ratio of hydrogen peroxide to P-metal modulating compound in the solution is from 2:1 to 200:1, from 3:1 to 100:1 and from 10:1 to 50:1.

For example, an aqueous, peroxide disinfecting solution comprising 3.0 wt. % hydrogen peroxide (MW=34 g/mol) and 0.35 wt. % of the P-metal modulating compound, urea ((MW=60 g/mol) will have a molar concentration of hydrogen peroxide and urea of $8.8\times10^{-3}$ and $5.8\times10^{-4}$, respectively, based on the assumption that the aqueous solution has a density of 1 g/mL. Accordingly, the molar ratio of hydrogen peroxide to urea is $8.8\times10^{-3}/5.8\times10^{-4}$ or approximately 15:1.

The molar ratio of hydrogen peroxide to P-metal modulating compound in the described peroxide lens care solutions can be important because the molar ratio can have some affect on the neutralization profile of the hydrogen peroxide with the neutralization catalyst. As stated, the enhanced biocidal activity of the described peroxide solutions is believed to result from slowing the rate of peroxide neutralization over the first one or two hours following contact of the peroxide solution with the neutralization catalyst. It is proposed that the P-metal modulating compound competes with the hydrogen peroxide for the active catalytic sites of the neutralization catalyst. One of skilled in the art would expect that this competition for the active catalytic sites of the catalyst is concentration dependent.

In contrast, one mole of urea hydrogen peroxide consists of one mole of hydrogen peroxide and one mole of urea to provide a peroxide solution with a molar ratio of 1:1. In fact, if one were to rely solely on the presence of urea hydrogen peroxide to achieve a fully dissociative peroxide concentration of 3 wt. % or greater, the relatively large amounts of urea in the formulation following neutralization of the peroxide would result in a solution with a very high osmolality value, most likely exceeding 500 mOsmol/kg. In other words, the neutralized solutions would cause significant discomfort to a patient if the disinfected contact lenses were to be inserted into the eyes without first rinsing the lenses, e.g., with a separate saline solution. See, Example section, infra. As shown, a disinfecting solution that contains just 3 wt. % urea hydrogen peroxide would contain about 1.9 wt % of urea and 1.1 wt % of hydrogen peroxide, and the osmolality of the solution following neutralization of the peroxide would be about 600 mOsmol/kg. Accordingly, the use of urea hydrogen peroxide as a sole source of hydrogen peroxide in a peroxide-based, contact lens disinfecting solution is of little interest, and is not an embodiment of Applicants' contact lens care solutions.

In one embodiment, the P-metal modulating compound is of general formula I

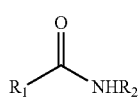

wherein $R_1$ is $C_1$-$C_6$alkyl, $-(CH_2)_nCH(^+NH_3)(CO_2^-)$ and n is 1 or 2, or $NHR_3$; and $R_3$ is H or $R_2$, and $R_2$ is H, OH or $C_1$-$C_6$alkyl. In a particular embodiment, the P-metal-modulating compound is urea, i.e., $R_1$ is $NHR_3$, $R_2$ and $R_3$ are both H. The term "$C_1$-$C_6$alkyl" includes a straight or branched alkyl and optionally one or more hydroxyl substituents. In many preferred embodiments, the P-metal modulating compound are present in the described peroxide solutions at a concentration from 0.01 wt. % to 2.0 wt. %, from 0.01 wt. % to 1.0 wt. %, from 0.05 wt. % to 0.6 wt. %, or from 0.08 wt. % to 0.4 wt %.

In another embodiment, the P-metal modulating compound is an amino acid or a compound derived from an amino acid. Exemplary amino acids are selected from the group consisting of methionine, aspargine, glutamine, histidine, lysine, arginine, glycine, serine, cystine and threonine. Cystine is an oxidized, disulfide form of cysteine. In many preferred embodiments, the amino acid, P-metal modulating compound are present in the described peroxide solutions at a concentration from 0.01 wt. % to 2.0 wt. %, from 0.05 wt. % to 0.6 wt. %, or from 0.08 wt. % to 0.4 wt. %.

In another embodiment, the P-metal modulating compound is a compound with one or two nitrogen atoms and one to six carbon atoms. A particular compound of this class is taurine. Other P-metal-modulating compounds include propionamide, isobutyramide, N-methyl-propionamide, 2-imidazolidinone and (2-hydroxyethyl)urea. Still another P-metal modulating compound is 2-amino-2-hydroxymethyl-1,3-propane diol, also referred to in the art as TRIS. In fact, the presence of TRIS in a peroxide solution can also contribute to the buffering capacity of the solution. In many preferred embodiments, these P-metal modulating compound are present in the described peroxide solutions at a concentration from 0.01 wt. % to 2.0 wt. %, from 0.05 wt. % to 0.6 wt. %, or from 0.08 wt. % to 0.4 wt. %.

As stated, the hydrogen peroxide is present at a concentration that is suitable for disinfecting a contact lens including soft and RGP lenses, and in particular, a silicone hydrogel contact lens, against a wide spectrum of microorganisms, including but not limited to Staphylococcus aureus, Pseudomonas aeruginosa, Serratia marcescens, Candida albicans, and Fusarium solani. The hydrogen peroxide is present from 0.5 wt. % to about 6 wt. %, from 2 wt. % to 4 wt. %, or about 3 wt. %. The amount of hydrogen peroxide in the solution is dependent upon a number of parameters including the type and concentration of the P-metal modulating compound present in the solution.

In many instances, the appropriate peroxide concentration is determined by the time it takes to neutralize the hydrogen peroxide to an ophthalmically safe level for a given catalytic element and for a particular P-metal modulating compound. Ideally, the residual peroxide content should be within an ophthalmically safe level preferably within less than about 8 hours, preferably less than about 6 hours, more preferably less than about 4 hours. By the term "ophthalmically safe" with respect to a contact-lens solution is meant that a contact lens treated with the solution is safe for direct placement on the eye without rinsing, that is, the solution is safe and sufficiently comfortable for daily contact with the eye via a contact lens. Although most patients can tolerate about 200 ppm of residual peroxide in a contact lens disinfecting solution, the target level of peroxide at or near complete neutralization is less than about 150 ppm, and most preferably less than about 100 ppm.

For a given concentration of hydrogen peroxide, the concentration of the P-metal modulating compound in the solution is dependent upon how strongly the P-metal modulating compound interacts with the neutralizing catalytic sites of the catalytic element. Though typically, the P-metal modulating compound is present in the described peroxide solutions at a concentration from 0.01 wt. % to 2.0 wt. %

Example No. 1

To a 500 mL sample of Clear Care® is added 1.625 g of urea to provide a modified Clear Care® formulation containing 0.325 wt. % urea.

Example No. 2

To a 500 mL sample of Clear Care® is added 1.625 g of urea and 50 mg of taurine to provide a modified Clear Care® formulation containing 0.325 wt. % urea and 100 ppm taurine.

Example No. 3A

To a 500 mL sample of Clear Care® is added 0.5 g of taurine to provide a modified Clear Care® formulation containing 0.1 wt. % taurine.

Example No. 3B

To a 500 mL sample of Clear Care® is added 1.0 g of taurine to provide a modified Clear Care® formulation containing 0.2 wt. % ppm taurine.

Comparative Ex. No. 1

Clear Care® manufactured by CibaVision, Inc. Using the assay method described herein we have determined the hydrogen peroxide concentration in Clear Care® to be from 3.3 wt. % to 3.5 wt. %.

Comparative Ex. No. 2

In accordance with U.S. Pat. No. 7,022,654, Applicants also prepared solutions containing: 0.077 wt. % sodium phosphate; 0.156 wt. % disodium phosphate; 0.79 wt. % NaCl; 0.05 wt. % Pluronic® 17R4 and 3.0 wt. % stabilized hydrogen peroxide. Applicants believe that this comparative example formulation is representative of the solution components and their respective concentration for Clear Care®.

Figure 5A:
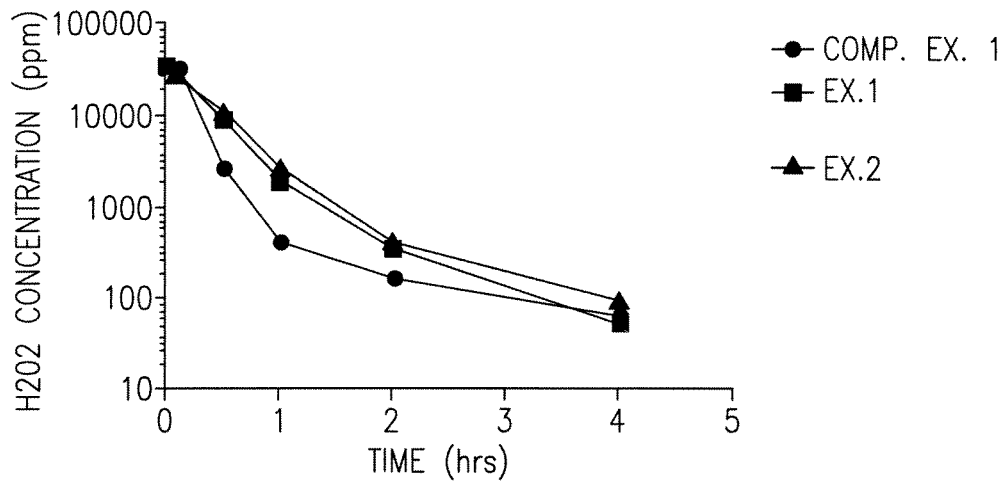
FIG. 5A is a plot of neutralization rate profiles of peroxide disinfecting solutions of the invention.

FIG. 5A is a peroxide neutralization plot for three solutions: Comparative Ex. No. 1, Example No. 1 and Example No. 2. As indicated by the plot data, the presence of the P-metal-modulating compounds urea, or urea with taurine, in a base peroxide disinfecting solution, in this case a commercial solution of Clear Care®, shows a significant reduction in the rate of peroxide neutralization over the initial two hours.

One of ordinary skill in the art understands that that rate of peroxide neutralization is also dependent upon the type or design of the hydrogen peroxide lens case, and in particular the design of the catalytic element that comprises a P-metal. All of the peroxide neutralization data described herein was obtained with a hydrogen peroxide lens case provided in a contact lens care product package sold as Clear Care® by CibaVision. The Clear Care® product packages with the included lens case were purchased in the United States in 2009-10. Each of the hydrogen peroxide neutralization profiles and rate constants (as well as calculated the half-lives) stated herein and in the claims were obtained with a Clear Care® lens case. Also, the observed improvement in the log-kill biocidal data stated herein and in the claims was obtained with a Clear Care® lens case. Accordingly, the term "as measured in a given hydrogen peroxide, contact lens disinfection case equipped with a catalyst comprising a P-metal" refers to a hydrogen peroxide lens case provided in a contact lens care product package sold as Clear Care® by CibaVision in the United States in 2009-10.

Figure 5B:
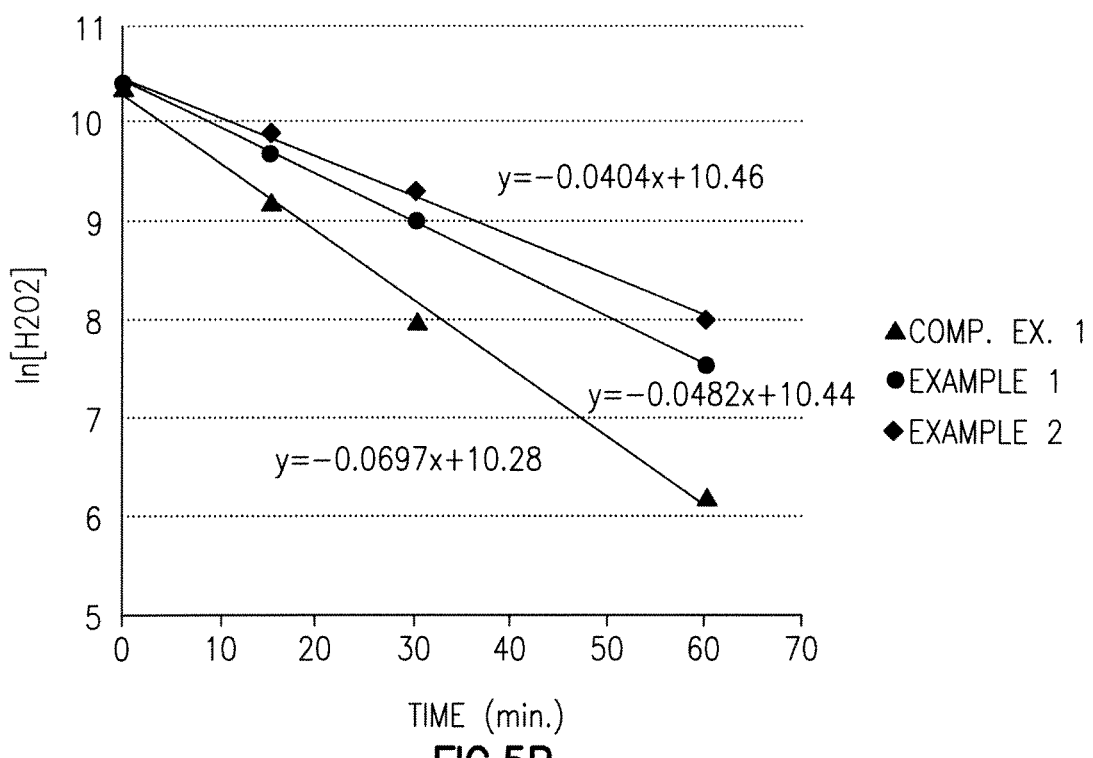
FIG. 5B is a graphical representation for determining the pseudo first-order rate constants for the neutralization of hydrogen peroxide disinfecting solutions of FIG. 5A.

The line plots shown in FIG. 5B is determined from the peroxide neutralization data of FIG. 5A over the initial 60 minutes, i.e. at time of 0, 5 min, 15 min, 30 min and 60 min. The line plots are pseudo first-order plots indicating the rate of decomposition of the hydrogen peroxide for each of the tested solutions. The pseudo first-order rate constant is determined from the slope of the line plots. The pseudo first-order rate constants are tabulated below along with the corresponding half-life ($\tau_{1/2}$) values: $\tau_{1/2}=\ln(2)/k$.

| Solution | k (min$^{-1}$) | $\tau_{1/2}$ (min) |
|---|---|---|
| Comp. Ex. 1 | 0.07 | 9.90 |
| Example 1 | 0.048 | 14.4 |
| Example 2 | 0.04 | 17.3 |

Accordingly, one embodiment of the invention is directed to a contact lens disinfecting solution comprising: 0.5 wt. % to 6 wt. % hydrogen peroxide or a chemical precursor of hydrogen peroxide; and a P-metal modulating compound. The solution exhibits a pseudo first-order, half-life of hydrogen peroxide over an initial sixty minutes of neutralization from 12 minutes to 30 minutes, as measured in a given hydrogen peroxide, contact lens disinfection case equipped with a catalyst comprising a P-metal. Exemplary peroxide disinfecting solutions of the invention will have a pseudo first-order, half-life of hydrogen peroxide over the initial sixty minutes of neutralization from 14 minutes to 22 minutes. It is preferred that the concentration of hydrogen peroxide after an initial six hours of neutralization is less than 150 ppm.

The peroxide neutralization plot for three solutions: Comparative Ex. No. 1, Example No. 3A and Example No. 3B are very similar to those observed in FIG. 5A. As indicated by the plot data, the presence of the P-metal modulating compounds taurine, in a base peroxide disinfecting solution, in this case a commercial solution of Clear Care®, shows a significant reduction in the rate of peroxide neutralization over the initial two hours of neutralization. The data also indicates there is very little difference if any with respect to the rate of peroxide neutralization at the two concentrations of taurine.

Example 4A

A solution was prepared containing the stated components of Comparative Example No. 2 plus 0.49 wt. % urea.

Example 4B

A solution was prepared containing the stated components of Comparative Example No. 2 plus 0.75 wt. % urea hydrogen peroxide (0.48 wt. % urea) and 6 ppm of branched lauramine oxide.

Figure 6A:
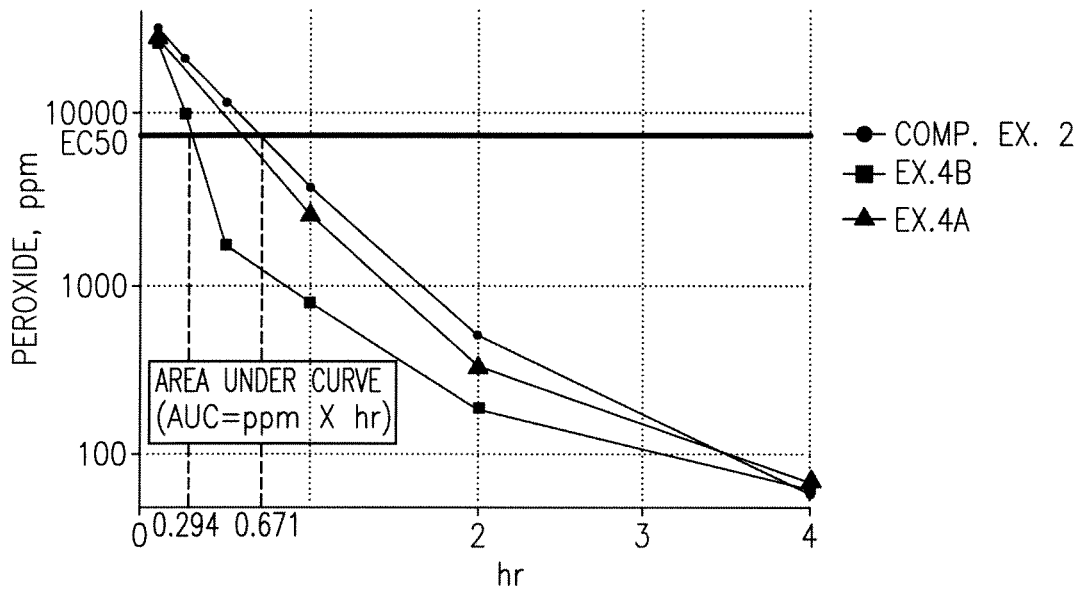
FIG. 6A is a plot of neutralization rate profiles of peroxide disinfecting solutions of the invention.
Figure 6B:
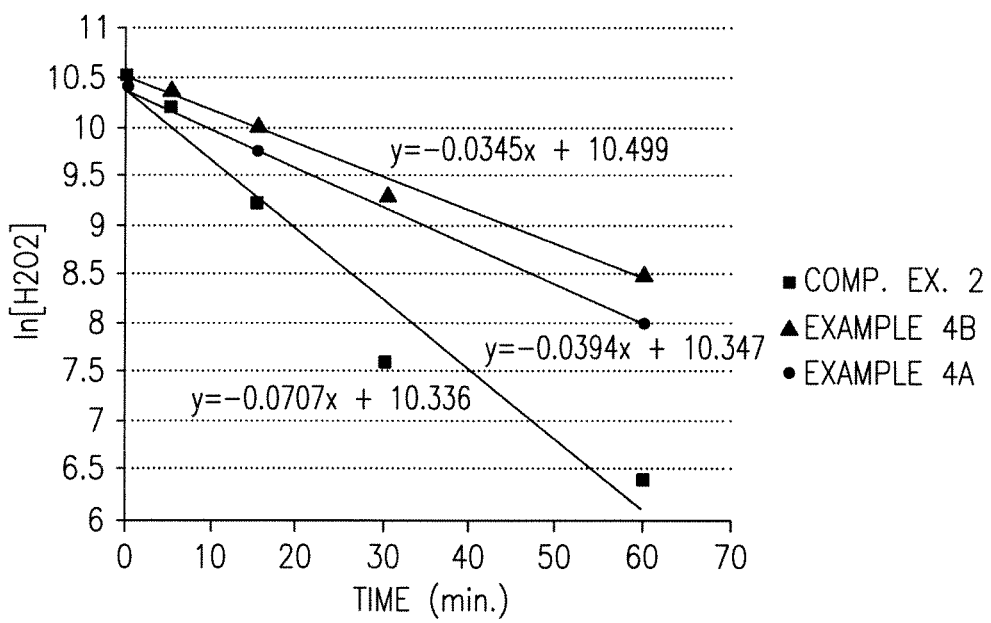
FIG. 6B is a graphical representation for determining the pseudo first-order rate constants for the neutralization of hydrogen peroxide disinfecting solutions of FIG. 6A.

FIG. 6A is a peroxide neutralization plot for three solutions: Comparative Ex. No. 2, Example No. 4A and Example No. 4B. As indicated by the plot data, the presence of the P-metal modulating compounds urea, provided by adding urea or urea hydrogen peroxide to a base peroxide disinfecting solution shows a significant reduction in the rate of peroxide neutralization over an initial two hours of neutralization. The line plots shown in FIG. 6B is determined from the peroxide neutralization data of FIG. 6A over the initial 60 minutes, i.e. at time of 0, 5 min, 15 min, 30 min and 60 min. The pseudo first-order rate constants are tabulated below along with the corresponding half-life ($\tau_{1/2}$) values: $\tau_{1/2}=\ln(2)/k$.

| Solution | k (min$^{-1}$) | $\tau_{1/2}$ (min) |
|---|---|---|
| Comp. Ex. 1 | 0.071 | 9.90 |
| Example 4A | 0.039 | 17.8 |
| Example 4B | 0.035 | 19.8 |

The peroxide neutralization rate profiles of select disinfecting solutions were determined as follows. Each solution (10 mL) was placed in a peroxide contact lens container supplied with the Clear Care® peroxide solution. The top cap portion equipped with a platinum element is then screwed to the container thereby submerging the platinum element into the solution. Immediate peroxide neutralization is observed with the evolution of gas. Aliquots of the solution are removed at the stated time points and the concentration of hydrogen peroxide is determined by known analytical methods.

The aliquots of solution are titrated with 0.1N potassium permanganate in the presence of an acidic aqueous solution. To perform this titration, a Mettler Toledo Titration Excellence T50 System (Mettler Toledo, Columbus, Ohio) is used. A 3.0 ml, aliquot of sample is added to 60 mL of water and 1.25 mL of 20% sulfuric acid solution. The sample is placed in the system and analyzed using a built-in hydrogen peroxide determination method. A Mettler Toledo Plug & Play DMi140-SC Platinum Ring Electrode (Mettler Toledo, Columbus, Ohio) is used to determine the electrochemical equivalence endpoint of the titration. Once an endpoint is determined the instrument calculates the hydrogen peroxide concentration of the sample. The determined peroxide concentrations are used to provide the peroxide neutralization plots.

Of course, contact lens disinfecting solutions containing hydrogen peroxide, or a chemical precursor of hydrogen peroxide, will also include other solution components including one or more surfactants to assist in the removal of denatured tear proteins and environmental containments, one or more buffer components to maintain the solution in an ophthalmically acceptable pH range, and one or more tonicity agents to adjust the osmolality of the solution. The contact lens solution can also include one or more comfort components to provide lubrication or a moisturizing affect to a disinfected contact lens.

Suitable surfactants can be generally described as block copolymers of a hydrophile and hydrophobe terminated in either primary or secondary hydroxyl groups. A first example of such surfactants are polyoxyethylene/polyoxypropylene condensation polymers. Such block copolymers can be obtained commercially from the BASF Corporation under the trademark Pluronic®. Low foaming surfactants are particularly applicable in peroxide-based solutions. A particular polyoxyethylene/polyoxypropylene condensation polymer is prepared by first synthesizing a polyoxyethylene chain of desired molecular weight by the controlled addition of ethylene oxide to ethylene glycol. In the second step of the synthesis, propylene oxide is added to create hydrophobic blocks on the outside of the molecule. Such block copolymers can be obtained commercially from the BASF Corporation under the trademark Pluronic® R, and are generally known in the art as low foam surfactants. The letter R found in the middle of the designation of the Pluronic® R series signifies that this product has a reverse structure compared to the Pluronic® products, i.e., the hydrophile (ethylene oxide) is sandwiched between the propylene oxide blocks.

The concentration of a surfactant component in the lens care peroxide solution varies over a wide range depending on a number of factors, for example, the specific surfactant or surfactants being used, and the other components in the solution. Often the amount of surfactant is in the range of 0.005 wt. % to 0.8 wt. %, or from 0.01 wt. % to 0.5 wt. %. Preferably, the surfactant is present in an amount less than 0.2 wt. %; and most preferably less than 0.1 wt. %.

The sequence and percent distribution of hydrophobic and hydrophilic segments in these block copolymers leads to important differences in surfactant properties. The surfactant is preferably a liquid at 20° C. The molecular weight of the polyoxypropylene block is preferably from 1000 to 2500. Most preferably, the molecular weight of the polyoxypropylene block is approximately 1700. Specific examples of Pluronic® surfactants that are satisfactory include: Pluronic® L42, Pluronic® L43, Pluronic® L61 and Pluronic® L81. Specific examples of Pluronic® R surfactants that are satisfactory include: Pluronic® 31R1, Pluronic® 31R2, Pluronic® 25R1, Pluronic® 17R1, Pluronic® 17R2, Pluronic® 12R3. Particularly good results are obtained with Pluronic® 17R4 surfactant and Pluronic® L81.

When selecting the structure of a block copolymer surfactant, it is preferred to select a surfactant that limits the amount of foaming of the solution because many surfactants will cause excessive foaming as oxygen is generated by the decomposition of the hydrogen peroxide upon contact with the catalytic disk. Block copolymers with low ethylene oxide content are the most effective defoamers. Within each series of block copolymer products, defoaming performance increases as ethylene oxide content decreases and molecular weight increases. The tendency of a surfactant to create and/or sustain foam is measured according to the Ross-Miles test protocol ASTM designation D-1173-53 (0.1%, at 50° C.). Moreover, one of ordinary skill in the art could easily identify, and therefore select, low foam Pluronic®-type surfactants merely by reviewing the Tables of surfactant properties in a product brochure, Surfactants, Pluronics & Tetronics, BASF Corporation 1999, pp. 24-31.

The composition of the present invention preferably contains a hydrogen peroxide stabilizer. Preferably, the stabilizer is a diphosphonic acid alkanol as disclosed in U.S. Pat. No. 4,812,173. The most preferred stabilizer is diethylene triamine penta-(methylenephosphonic acid) or a physiologically compatible salt thereof. This compound is manufactured by Solutia under the name DEQUEST®2060. The stabilizer is preferably present in the solution in an amount between about 0.001 and about 0.03% by weight of the composition, and most preferably between about 0.006 and about 0.0120% by weight of the solution. Stabilization of hydrogen peroxide in contact lens disinfection systems is described in more detail in U.S. Pat. Nos. 4,812,173 and 4,889,689. The stabilized form of hydrogen peroxide used in the Example formulations described herein was obtained from Solvay Chemicals, Inc. If desired, additional conventional stabilizers may be employed in conjunction with or in place of the diethylene triamine penta-(methylenephosphonic acid) if it is compatible with the material to be sterilized.

The composition of the present invention very likely will include a buffer. The buffer maintains the pH preferably in the desired range, for example, in a physiologically acceptable range of about 5 to about 8. The buffer is selected from inorganic or organic bases, and includes phosphates, borates, citrates, nitrates, sulfates, carbonates, amino alcohols such as TRIS and BisTRIS, bicarbonates and mixtures thereof, more preferably basic phosphates, borates, citrates, tartrates, carbonates, bicarbonates and mixtures thereof. Typically, the buffer components are present in the described solutions from 0.001 wt. % to 2 wt. %, preferably 0.01 wt. % to 1 wt. %; most preferably from 0.05 wt. % to 0.50 wt. %. As stated, the amino alcohol buffer components can also function as P-metal-modulating agents. Phosphate and amino alcohol buffer components are two of the more preferred buffers.

In the case of a phosphate-based buffer system one or more phosphate buffer components, for example, combinations of monobasic phosphates, dibasic phosphates and the like can be used. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$), and potassium monobasic phosphate ($KH_2PO_4$).

The solutions of the present invention preferably include an effective amount of a tonicity component to provide the liquid medium with the desired tonicity. Such tonicity components may be present in the solution and/or may be introduced into the solution. Among the suitable tonicity adjusting components that may be employed are those conventionally used in contact lens care products, such as various inorganic salts. Sodium chloride and/or potassium chloride and the like are very useful tonicity components. The amount of tonicity component included is effective to provide the desired degree of tonicity to the solution. Such amount may, for example, be in the range of about 0.4% to about 1.5% (w/v). For example, sodium chloride can be present in the range of 0.50% to 0.90% (w/v).

The described solutions can also include a wetting agent to help maintain the lens in a moistened condition and to help with initial comfort upon placement of the disinfected contact lens upon the eye. Exemplary wetting agents include propylene glycol, glycerin and dexpanthenol. The wetting agents are generally present in the solution at a concentration from 0.2 wt. % to 1.5 wt. %.

The additional non-limiting examples illustrate certain aspects of the present invention.

Examples 5 to 9

The following peroxide contact lens care solutions were prepared by adding the appropriate amounts of each of the listed components to purified water, see Table 1. The pH is adjusted to about 6.7 with appropriate amounts of hydrochloric acid or sodium hydroxide.

As expected, the peroxide formulations containing slightly greater amounts of hydrogen peroxide exhibited higher biocidal activity against the fungi, *C. albicans* and *F. solani*. In fact, the biocidal efficacy against *C. albicans* for Example Nos. 7 to 9 exceeded the market leader peroxide disinfecting solution by greater than 100-fold. Also, Example 9 exhibits a near 10-fold greater kill against *F. solani* at 6 and 24 hours over Clear Care®. See, Table 2. The control solution is Clear Care® (3.3 to 3.5 wt. % hydrogen peroxide).

TABLE 1

| | Example No. | | | | | |
|---|---|---|---|---|---|---|
| | 5 | 6 | 7 | 8 | 9 | 10 |
| Na phosphate, dibasic | 0.55 | 0.55 | 0.55 | 0.55 | 0.55 | 0.55 |
| citric acid | 0.15 | 0.15 | 0.15 | 0.15 | 0.15 | 0.15 |
| KCl | 0.1 | 0.1 | 0.1 | 0.1 | 0.1 | 0.1 |
| propylene glycol | 1.0 | 1.0 | 1.0 | 1.0 | 1.0 | 1.0 |
| Poloxamer L81 | 0.006 | 0.006 | 0.006 | 0.006 | 0.006 | 0.006 |
| urea | 0.32 | 0.32 | 0.32 | 0.32 | 0.32 | 0.32 |
| lauramine oxide (ppm) | — | — | 10 | 10 | 10 | 10 |
| hydrogen peroxide$^a$ | 3.0 | 3.3 | 3.0 | 3.2 | 3.5 | 3.2 |
| taurine (ppm) | — | — | — | — | — | 100 |

ISO Biocidal Stand-Alone Data

In order to assess the biocidal activity of a particular lens care solution Applicants use the "Stand-Alone Procedure for Disinfecting Products" based on the Disinfection Efficacy Testing for Products dated May 1, 1997, prepared by the U.S. Food and Drug Administration, Division of Ophthalmic Devices. This performance requirement does not contain a rub procedure. The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per ml must be reduced by a mean value of not less than 1.0 log within the minimum recommended disinfection time with no increase at four times the minimum recommended disinfection time.

The antimicrobial efficacy of each of the various compositions for the chemical disinfection and cleaning of contact lenses are evaluated in the presence of 10% organic soil using the stand-alone procedure. Microbial challenge inoculums are prepared using *Staphylococcus aureus* (ATCC 6538), *Pseudomonas aeruginosa* (ATCC 9027), *Serratia marcescens* (ATCC 13880), *Candida albicans* (ATCC 10231) and *Fusarium solani* (ATCC 36031). The test organisms are cultured on appropriate agar and the cultures are harvested using sterile Dulbecco's Phosphate Buffered Saline plus 0.05 percent weight/volume polysorbate 80 (DPBST) or a suitable diluent and transferred to a suitable vessel. Spore suspensions are filtered through sterile glass wool to remove hyphal fragments. *Serratia marcescens*, as appropriate, is filtered through a 1.2 μm filter to clarify the suspension.

After harvesting, the suspension is centrifuged at no more than 5000×g for a maximum of 30 minutes at a temperature of 20° C. to 25° C. The supernatant is decanted and resuspended in DPBST or other suitable diluent. The suspension is centrifuged a second time, and resuspended in DPBST or other suitable diluent. All challenge bacterial and fungal cell suspensions are adjusted with DPBST or other suitable diluent to $1 \times 10^7$ to $1 \times 10^8$ cfu/mL. The appropriate cell concentration may be estimated by measuring the turbidity of the suspension, for example, using a spectrophotometer at a preselected wavelength, for example, 490 nm. A peroxide lens disinfecting case provided with the Clear Care® product package containing a minimum of 10 mL of test solution per challenge organism is prepared. Each peroxide disinfecting case containing the solution to be tested is inoculated with a suspension of the test organism sufficient to provide a final count of $1 \times 10^5$ to $1 \times 10^6$ cfu/mL, the volume of the inoculum not exceeding 1 percent of the sample volume. Dispersion of the inoculum is ensured by vortexing the sample for at least 15 seconds. The inoculated product is stored at 10° C. to 25° C. Aliquots in the amount of 1.0 mL are taken of the inoculated product for determination of viable counts after certain time periods of disinfection.

The suspension is mixed well by vortexing vigorously for at least 5 sec. The 1.0 mL aliquots removed at the specified time intervals are subjected to a suitable series of decimal dilutions in validated neutralizing media. The suspensions are mixed vigorously and incubated for a suitable period of time to allow for neutralization of the microbial agent. The viable count of organisms is determined in appropriate dilutions by preparation of triplicate plates of trypticase soy agar (TSA) for bacteria and Sabouraud dextrose agar (SDA) for mold and yeast. The bacterial recovery plates are incubated at 30° C. to 35° C. for two to four days. The yeast recovery plates are incubated at 20° C. to 30° C. for two to four days. The mold recovery plates are incubated at 20° C. to 25° C. for three to seven days. The average number of colony forming units is determined on countable plates. Countable plates refer to 30 to 300 cfu/plates for bacteria and yeast, and 8 to 80 cfu/plate for mold except when colonies are observed only for the $10^0$ or $10^{-1}$ dilution plates. The microbial reduction is then calculated at the specified time points.

In order to demonstrate the suitability of the medium used for growth of the test organisms and to provide an estimation of the initial inoculum concentration, inoculum controls are prepared by dispersing an identical aliquot of the inoculum into a suitable diluent, for example, DPBST, using the same volume of diluent used to suspend the organism as listed above. Following inoculation in a validated neutralizing broth and incubation for an appropriate period of time, the inoculum control must be between $1.0 \times 10^5$ and $1.0 \times 10^6$ cfu/mL.

TABLE 2

Biocidal data at 6 and 24 hours.

|  | control | 7 | 8 | 9 |
|---|---|---|---|---|
| Biocidal (6 hours) | | | | |
| S. marcescens | 4.6 | >4.6 | >4.6 | >4.6 |
| C. albicans | 2.6 | 4.5 | 4.4 | >4.9 |
| F. solani | 2.7 | 2.7 | 3.0 | 3.6 |
| Biocidal (24 hours) | | | | |
| S. marcescens | 4.2 | >4.6 | >4.6 | >4.6 |
| C. albicans | 2.8 | 4.1 | 4.4 | >4.9 |
| F. solani | 2.7 | 2.8 | 3.2 | 3.5 |

A disinfection test study known in the art as "Regimen" was conducted on Example 7 to determine preservative effectiveness of the solutions following complete or near complete neutralization of the peroxide in the solutions. Commercial lenses selected from Softlens® 38, AcuVue®2 and Purevision® were used in the study. The results are reported in Table 3. Passing criteria is NMT 10 average CFU/lens for each lens type.

TABLE 3

| time | S. marcescens | C. albicans | F. solani |
|---|---|---|---|
| 6 hr | Pass | Pass | Pass |
| 7 days | Pass | Pass | Pass |
| 14 days | Pass | Pass | Pass |
| Comp. Ex. 1 7 days | Pass | Pass | Pass |

Figure 7:
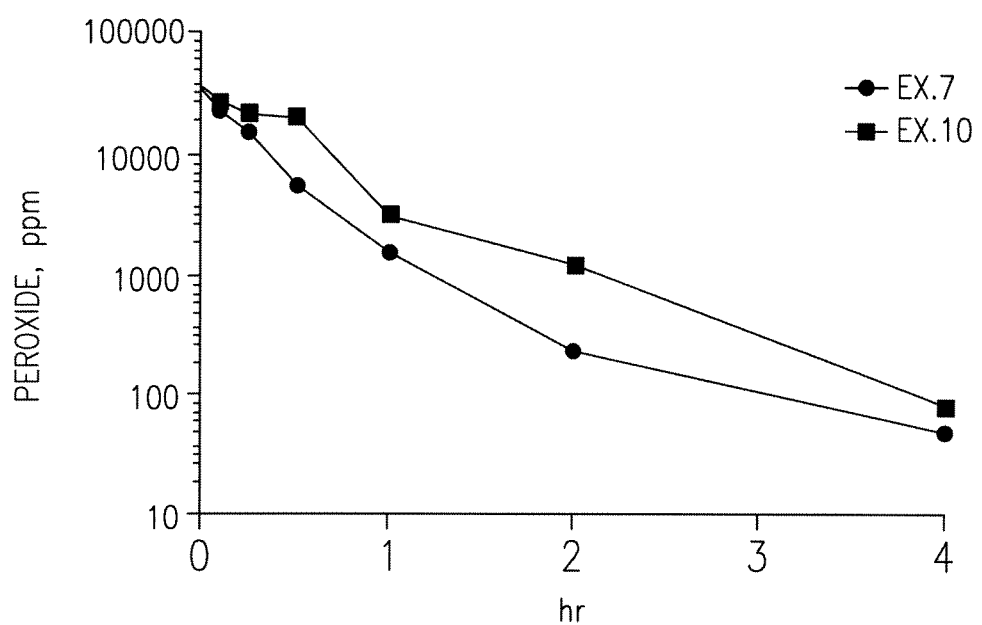
FIG. 7 is a plot of neutralization rate profiles of peroxide disinfecting solutions of the invention.

Applicants have also observed that certain P-metal modulating compounds at a given concentration can completely shut down the neutralization reaction. Thiourea at a concentration of 0.3 wt. % is one such compound. In contrast, taurine at a concentration of 100 ppm exhibits a very small effect on the rate of peroxide neutralization, yet if the concentration of taurine is increased to 0.1 wt. % or 1000 ppm a much greater reduction in the rate of peroxide neutralization is observed. Surprisingly, 100 ppm of taurine in combination with urea (0.325 wt. %) provides a further reduction in the neutralization rate than an identical solution containing the same amount of urea but without the taurine. See, FIG. 7. Accordingly, a particular peroxide disinfecting solution of interest will include urea or taurine alone, or a combination of urea and taurine.

Examples 11 to 14

The following peroxide contact lens care solutions were prepared by adding the appropriate amounts of each of the listed components to purified water. The amounts of sodium phosphate, citric acid, potassium chloride, propylene glycol, lauraamine oxide and poloxamer L81 in each Example formulation are as reported in Example 7 above. The concentration of a P-metal modulating compound, in this case, urea, was varied in each example formulation to determine if any difference in biocidal effectiveness of the formulations would be observed, Table 4. Again, the pH is adjusted to about 6.7 with appropriate amounts of hydrochloric acid or sodium hydroxide.

TABLE 4

| | Example No. | | | |
|---|---|---|---|---|
| | 11 | 12 | 13 | 14 |
| urea | — | 0.1 | 0.325 | 0.5 |
| hydrogen peroxide | 2.8 | 2.8 | 2.8 | 2.8 |
| Biocidal (6 hours) | | | | |
| S. marcescens | 4.5 | 4.5 | >4.5 | >4.5 |
| C. albicans | 2.6 | 4.2 | 4.7 | 4.7 |
| F. solani | 1.4 | 1.8 | 2.5 | 2.1 |
| Biocidal (24 hours) | | | | |
| S. marcescens | 4.5 | 4.5 | >4.5 | >4.5 |
| C. albicans | 2.7 | 3.8 | 4.3 | 4.4 |
| F. solani | 1.5 | 1.6 | 2.5 | 2.0 |

Examples 15 to 21

The following peroxide contact lens care solutions are prepared by adding the appropriate amounts of each of the listed components to purified water. The amounts of sodium phosphate, citric acid, potassium chloride, poloxamer L81 and hydrogen peroxide in each Example formulation are as reported in Example 7 above, Table 5.

TABLE 5

| | Example No. | | | | | | |
|---|---|---|---|---|---|---|---|
| | 15 | 16 | 17 | 18 | 19 | 20 | 21 |
| urea | 0.35 | — | 0.25 | — | 0.25 | — | 0.25 |
| taurine | — | 0.25 | 0.1 | — | — | — | — |
| glutamine | — | — | — | 0.2 | 0.1 | — | — |
| asparagine | — | — | — | — | — | 0.2 | 0.1 |

Examples 22 to 26

The following peroxide contact lens care solutions are prepared by adding the appropriate amounts of each of the listed components to purified water. The amounts of sodium phosphate, citric acid, potassium chloride, poloxamer L81 and hydrogen peroxide in each Example formulation are as reported in Example 7 above, Table 6.

TABLE 6

| | Example No. | | | | |
|---|---|---|---|---|---|
| | 22 | 23 | 24 | 25 | 26 |
| propionamide | 0.35 | — | — | — | — |
| isobutyramide | — | 0.35 | — | — | — |
| N-methyl-propionamide | — | — | 0.35 | — | — |
| 2-imidazolidinone | — | — | — | 0.35 | — |
| (2-hydroxyethyl)urea | — | — | — | — | 0.35 |

Example 27

The amino acid, L-lysine, was added to a commercial solution of Clear Care® peroxide disinfecting solution (500 mL) manufactured by CibaVision, Inc. to provide a contact lens care disinfecting solution containing 0.2 wt. % L-lysine.

Example 28

The amino acid, L-glutamine, was added to a commercial solution of Clear Care® peroxide disinfecting solution (500 mL) manufactured by CibaVision, Inc. to provide a contact lens care disinfecting solution containing 0.2 wt. % L-glutamine.

Figure 8A:
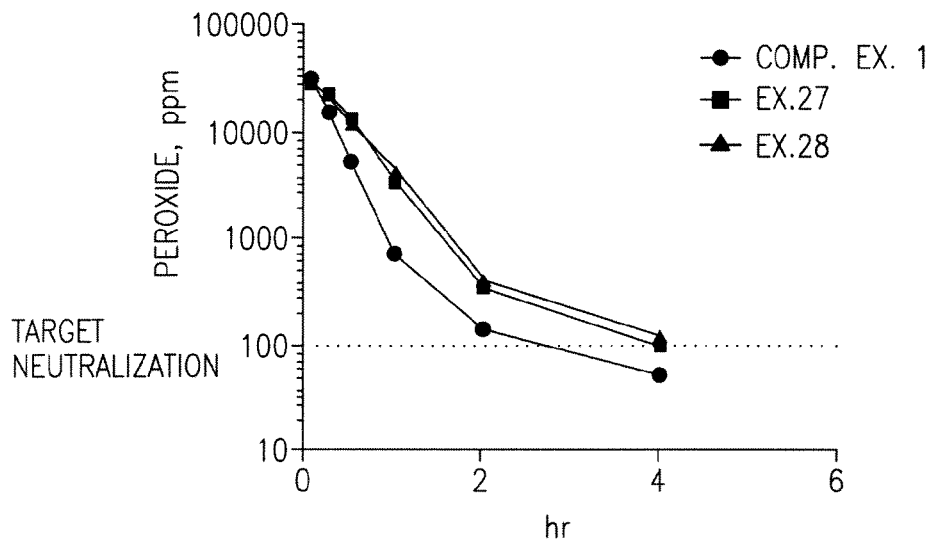
FIG. 8A is a plot of neutralization rate profiles of peroxide disinfecting solutions of the invention.

As indicated by the data plot of FIG. 8A, the presence of the amino acids in the peroxide disinfecting solutions of Examples 27 and 28 cause a reduction in the neutralization rate of the peroxide by the P-metal catalyst over the initial four hours. This decrease in neutralization rate leads to the observed increase in biocidal efficacy for the solutions as reported in Table 7. Examples 27 and 28 both exhibit a significant enhancement in disinfection efficacy against *S. marcescens*, and a very slight enhancement over the fungi, relative to the control solution Clear Care®.

TABLE 7

| Ex. No | time (hrs) | Sa | Ca | Fs |
|---|---|---|---|---|
| Comp. Ex. 1 | 4 | 3.9 | 4.5 | 3.8 |
| | 24 | ND | 4.7 | 4.1 |
| 27 | 4 | 4.4 | >4.7 | 4.1 |
| | 24 | ND | >4.7 | >4.7 |
| 28 | 4 | >4.6 | >4.7 | >4.1 |
| | 24 | ND | >4.7 | >4.1 |

Figure 8B:
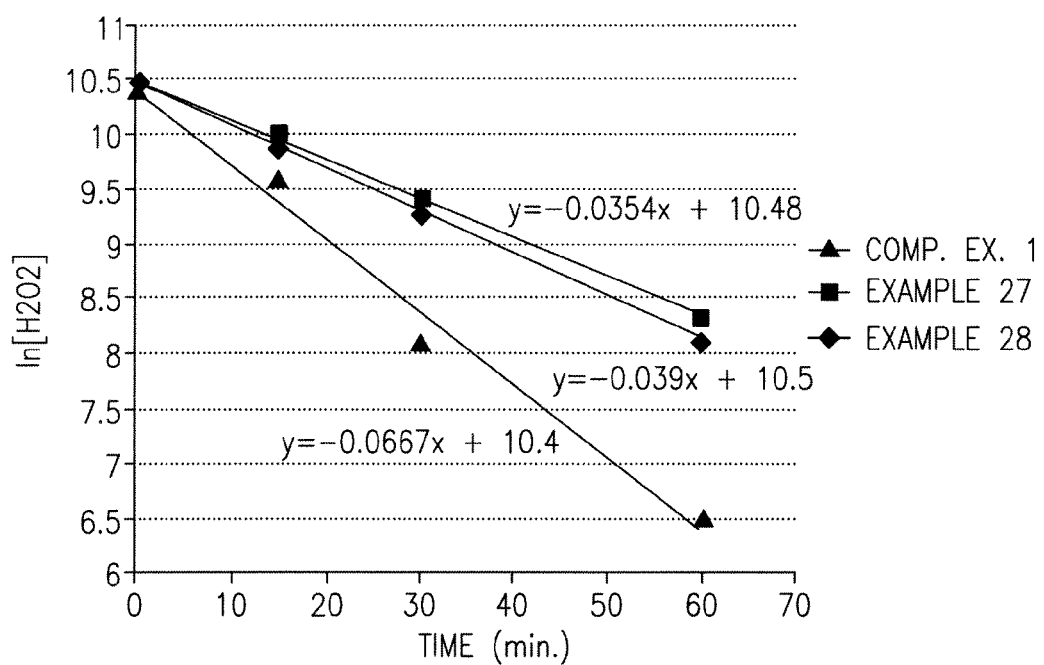
FIG. 8B is a graphical representation for determining the pseudo first-order rate constants for the neutralization of hydrogen peroxide disinfecting solutions of FIG. 8A.

The line plots shown in FIG. 8B is determined from the peroxide neutralization data of FIG. 8A over the initial 60 minutes, i.e. at time of 0, 5 min, 15 min, 30 min and 60 min. again, the line plots are pseudo first-order plots indicating the rate of decomposition of the hydrogen peroxide for each of the tested solutions. The pseudo first-order rate constants are tabulated below along with the corresponding half-life ($\tau_{1/2}$) values.

| Solution | k (min$^{-1}$) | $\tau_{1/2}$ (min) |
|---|---|---|
| Comp. Ex. 1 | 0.068 | 10.2 |
| Example 27 | 0.035 | 19.8 |
| Example 28 | 0.039 | 17.8 |

Examples 29 to 34

The following peroxide contact lens care solutions are prepared by adding the appropriate amounts of each of the listed components to purified water. The amounts of sodium phosphate, citric acid, potassium chloride, poloxamer L81 and hydrogen peroxide in each Example formulation are as reported in Example 7 above, Table 8.

TABLE 8

| | Example No. | | | | | |
|---|---|---|---|---|---|---|
| | 29 | 30 | 31 | 32 | 33 | 34 |
| urea | — | 0.25 | — | 0.25 | — | 0.25 |
| lysine | 0.2 | 0.1 | — | — | — | — |
| histidine | — | — | 0.2 | 0.1 | — | — |
| aspartic acid | — | — | — | — | 0.2 | 0.1 |

Comparative Examples 3 to 5

Several comparative lens care disinfecting solutions were prepared with urea hydrogen peroxide as a sole source of hydrogen peroxide, see Table 9. As indicated by the osmolality of the solutions following peroxide neutralization, the solutions would cause significant discomfort to a patient if such solutions were to come in direct contact with ocular tissue.

TABLE 9

| | Comparative Ex. No. | | |
|---|---|---|---|
| | 3 | 4 | 5 |
| Na phosphate, dibasic | 0.4 | 0.4 | 0.4 |
| citric acid | 0.15 | 0.15 | 0.15 |
| KCl | 0.2 | 0.2 | 0.2 |
| propylene glycol | 1.0 | 1.0 | 1.0 |
| hyaluronic acid | 0.1 | 0.1 | 0.1 |
| Dequest ® 2016 | 0.1 | 0.1 | 0.1 |
| urea hydrogen peroxide | 3.0 | 5.0 | 7.0 |
| (wt. % H$_2$O$_2$) | (1.1) | (1.8) | (2.5) |
| osmolality after peroxide neutralization (mOsmol/kg) | 606 | 837 | 1061 |

Example 35

Figure 9A:
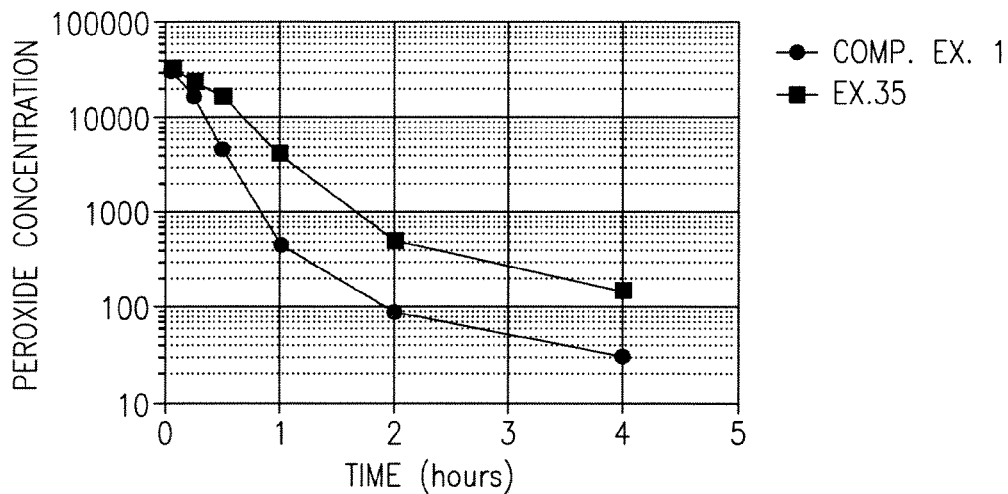
FIG. 9A is a plot of neutralization rate profiles of peroxide disinfecting solutions of the invention.
Figure 9B:
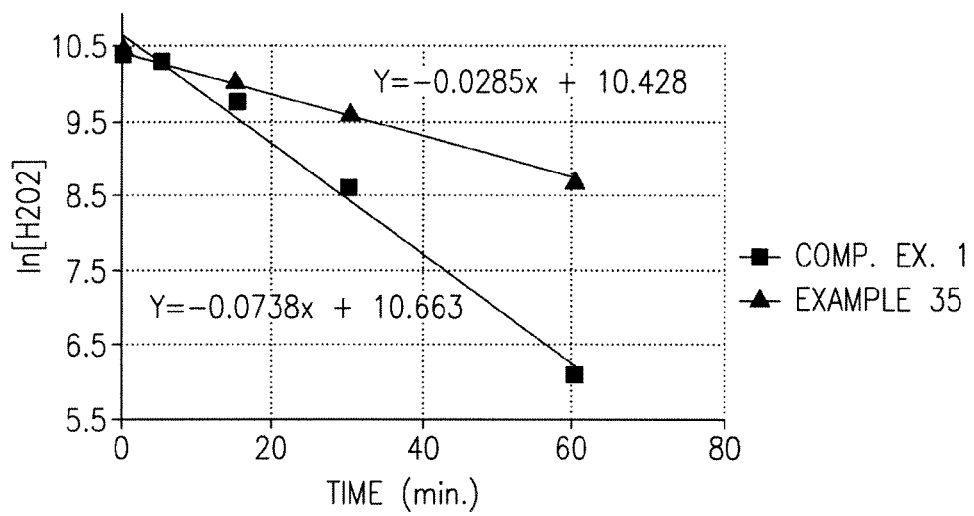
FIG. 9B is a graphical representation for determining the pseudo first-order rate constants for the neutralization of hydrogen peroxide disinfecting solutions of FIG. 9A.

A peroxide disinfecting solution comprising 3.2 wt. % hydrogen peroxide, 0.12 wt. % TRIS, 0.15 wt. % citric acid, 0.79 wt. % NaCl and 0.05 wt. % Pluronic® 17R4 was prepared. The solution was formulated to model a commercial Clear Care® solution except for the substitution of TRIS buffer for the phosphate buffer. FIG. 9A is a peroxide neutralization plot for two solutions: Comparative Ex. No. 1, Example No. 35. As indicated by the plot data, the presence of the P-metal modulating compounds TRIS in a base peroxide disinfecting solution, in this case a commercial solution of Clear Care®, shows a significant reduction in the rate of peroxide neutralization over the initial two hours. The line plots shown in FIG. 9B is determined from the peroxide neutralization data of FIG. 9A over the initial 60 minutes, i.e. at time of 0, 5 min, 15 min, 30 min and 60 min. The pseudo first-order rate constants are tabulated below along with the corresponding half-life ($\tau_{1/2}$) values.

| Solution | k (min$^{-1}$) | $\tau_{1/2}$ (min) |
|---|---|---|
| Comp. Ex. 1 | 0.076 | 9.4 |
| Example 35 | 0.029 | 24 |

The invention is also directed to methods for treating a contact lens using the described lens care peroxide disinfecting solutions. Methods of cleaning and disinfecting contact lens with disinfecting solutions containing peroxide are well known and are included within the scope of the invention. Such methods comprise contacting a contact lens with such a composition at conditions effective to provide the desired treatment to the contact lens. Contacting at or about ambient temperature is very convenient and useful. The contacting preferably occurs at or about atmospheric pressure. The contacting preferably occurs for a time in the range of about 5 minutes or about 1 hour to about 12 hours or more. The contact lens can be contacted with the solution by immersing the lens in the solution.

In one embodiment, the invention is directed to a method of cleaning and disinfecting a contact lens. The method comprising instructing a consumer to disinfect their contact lens including the following steps: remove a contact from an eye and position the lens in a lens case that is equipped with a catalyst comprising a P-metal; and add a disinfection solution to the lens case such that the lens is submerged in the solution upon the closure of the lens case. The solution comprises 0.5 wt. % to 6 wt. % hydrogen peroxide or a chemical precursor of hydrogen peroxide, and a P-metal modulating compound. Also, the solution exhibits a pseudo first-order, half-life of hydrogen peroxide from 12 minutes to 30 minutes over an initial sixty minutes of neutralization following exposure of the disinfecting solution as measured in a given hydrogen peroxide, contact lens disinfection case equipped with a catalyst comprising a P-metal.

In another embodiment, the method as described above is used with a peroxide disinfecting solution comprising 0.5 wt. % to 6 wt. % hydrogen peroxide or a chemical precursor of hydrogen peroxide, and a P-metal modulating compound. The disinfecting solution exhibits a hydrogen peroxide neutralization profile that is more effective against *Candida albicans* or *Serratia marcescens* by 0.5 log-kill or greater after an initial four hours of neutralization with a catalyst comprising a P-metal than an equivalent contact lens disinfecting solution but without the P-metal modulating compound. Also, the disinfecting solution will have an osmolality value of less than 500 mOsmol/kg following neutralization of the hydrogen peroxide. As stated, the biocidal effectiveness of the described peroxide disinfection solution is measured in a given hydrogen peroxide, contact lens disinfection case equipped with a catalyst comprising a P-metal.

In yet another embodiment, the method as described above is used with a peroxide disinfecting solution comprising 0.5 wt. % to 6 wt. % hydrogen peroxide or a chemical precursor of hydrogen peroxide, and a P-metal modulating compound of general formula I

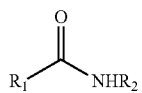

wherein $R_1$ is $C_1$-$C_6$alkyl, —$(CH_2)_n CH(^+NH_3)(CO_2^-)$ and n is 1 or 2, or $NHR_3$; and $R_3$ is H or $R_2$, and $R_2$ is H, OH or $C_1$-$C_6$alkyl; with the proviso that if $R_1$ is $NHR_3$ and $R_2$ and $R_3$ are H then the molar concentration of the P-metal modulating compound is less than the molar concentration of the hydrogen peroxide in the disinfecting solution.

In yet another embodiment, the method as described above is used with a peroxide disinfecting solution comprising 0.5 wt. % to 6 wt. % hydrogen peroxide or a chemical precursor of hydrogen peroxide, and a P-metal modulating compound with one or two nitrogen atoms and six or less carbon atoms. Also, the molar concentration of the P-metal modulating compound is less than the molar concentration of the hydrogen peroxide in the disinfecting solution.

In yet another embodiment, the method as described above is used with a peroxide disinfecting solution comprising 0.5 wt. % to 4 wt. % hydrogen peroxide or a chemical precursor of hydrogen peroxide, and a P-metal modulating compound. The solution exhibits a pseudo first-order, half-life of hydrogen peroxide over an initial sixty minutes of neutralization that is 1.25 times to 2.5 times greater with the P-metal modulating compound in the solution than in the absence of the P-metal modulating compound. The half-life value is determined for a given hydrogen peroxide, contact lens disinfection case equipped with a catalyst comprising a P-metal.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention.

We claim:

1. A contact lens disinfecting system comprising:
   a contact lens, peroxide disinfecting solution comprising 0.5 wt. % to 6 wt. % hydrogen peroxide or a chemical precursor of hydrogen peroxide; and a P-metal modulating compound, wherein the P-metal modulating compound is taurine, and the molar concentration of the P-metal modulating compound is less than the molar concentration of the hydrogen peroxide in the disinfecting solution; and
   a contact lens disinfecting apparatus comprising a container adapted to contain a quantity of the peroxide disinfecting solution, and a cap member that engages the container, the cap member including a lens supporting assembly that includes a lens support structure and a catalytic element that includes a P-metal, wherein the P-metal modulating compound is present at an effective concentration of 0.08 wt. %-2.0 wt. % such that the catalytic element catalyzes the decomposition of the hydrogen peroxide in the disinfecting solution with a pseudo first-order, half-life of hydrogen peroxide over an initial sixty minutes of neutralization that is 1.25 times to 3 times greater with the P-metal modulating compound in the solution than in the absence of the P-metal modulating compound, and wherein the pseudo first-order, half-life of hydrogen peroxide over an initial sixty minutes of neutralization is from 12 minutes to 30 minutes.

2. The disinfecting system of claim 1 wherein the pseudo first- order, half-life of hydrogen peroxide over the initial sixty minutes is from 14 minutes to 22 minutes, and the concentration of hydrogen peroxide after an initial six hours of neutralization is less than 150 ppm.

3. The disinfecting system of claim 1 wherein the disinfecting solution further comprises a low foam surfactant, particularly a polyoxyethylene/polyoxypropylene condensation polymer selected from the group consisting of Pluronic® L42, Pluronic® L43, Pluronic® L61, Pluronic® L81, Pluronic® 31R1, Pluronic® 31R2, Pluronic® 25R1, Pluronic® 17R1, Pluronic® 17R2, Pluronic® 12R3 and Pluronic® 17R4.

4. The disinfecting system of claim 1 wherein the P-modulating compound provides a hydrogen peroxide neutralization profile that is more effective against *Candida albicans* by 0.8 log-kill or greater after an initial four hours of neutralization than an equivalent contact lens disinfecting solution but without the P-metal modulating compound.

5. The disinfecting system of claim 1 wherein the P-metal-modulating compound is present at a concentration of from 0.08 wt. % to 1.0 wt. %.

6. The disinfecting system of claim 1 wherein the molar ratio of the hydrogen peroxide to the P-metal modulating compound is from 3:1 to 100:1.

7. A contact lens disinfecting system comprising:
   a contact lens, peroxide disinfecting solution comprising 0.5 wt. % to 6 wt. % hydrogen peroxide or a chemical precursor of hydrogen peroxide and a P-metal modulating compound, wherein the P-metal modulating compound is taurine, and
   a contact lens disinfecting apparatus comprising a container adapted to contain a quantity of the peroxide disinfecting solution, and a cap member that engages the container, the cap member including a lens supporting assembly that includes a lens support structure and a catalytic element that includes a P-metal, wherein the P-metal modulating compound is present at an effective concentration of 0.08 wt. %-2.0 wt. % such that the catalytic element catalyzes the decomposition of the hydrogen peroxide in the disinfecting solution with a pseudo first-order, half-life of hydrogen peroxide over an initial sixty minutes of neutralization that is 1.25 times to 3 times greater with the P-metal modulating compound in the solution than in the absence of the P-metal modulating compound.

8. The disinfecting system of claim 7 wherein the pseudo first-order, half-life of hydrogen peroxide over the initial sixty minutes of neutralization is from 1.25 times to 2 times greater with the P-metal modulating compound in the solution than in the absence of the P-metal modulating compound.

* * * * *